United States Patent [19]

Levinson et al.

[11] 4,028,408

[45] June 7, 1977

[54] NOVEL PREPARATION OF TRIFLUOROMETHYLTHIOACETIC ACID

[75] Inventors: Sidney Harry Levinson; Wilford Lee Mendelson, both of Philadelphia, Pa.

[73] Assignee: SmithKline Corporation, Philadelphia, Pa.

[22] Filed: Apr. 15, 1976

[21] Appl. No.: 677,190

[52] U.S. Cl. .................... 260/539 R; 260/609 R
[51] Int. Cl.² ............ C07C 149/16; C07C 153/017; C07C 148/00
[58] Field of Search .................. 260/539 R, 609 R

[56] References Cited

OTHER PUBLICATIONS

Harris et al., J. Org. Chem., 32, 2063–2074 (1967).

*Primary Examiner*—Jane S. Myers
*Attorney, Agent, or Firm*—William H. Edgerton; Alan D. Lourie; Richard D. Foggio

[57] ABSTRACT

Methods and intermediates are disclosed for the preparation of trifluoromethylthioacetic acid using the reaction of trifluoromethylsulfenyl halides with certain orthoesters.

12 Claims, No Drawings

NOVEL PREPARATION OF TRIFLUOROMETHYLTHIOACETIC ACID

This invention relates to a new preparation of the useful intermediate, trifluoromethylthioacetic acid, which gives good yields and involves no heavy metal chemical reactants.

Trifluoromethylthioacetic acid is used to prepare commercially useful 7-trifluoromethylmercaptoacetamidocephalosporins as described in U.S. Pat. No. 3,828,037. The intermediate is described there as being prepared by the reaction of trifluoromethylmercaptan silver salt and iodoacetic acid at room temperature for eleven days, see for example column 2, lines 54–60. Obviously on a commercial basis an alternative which uses less expensive reactants and more suitable reaction conditions is desirable.

We have now found that trifluoromethylsulfenyl halides, especially the chloride, react easily and in good yield with trimethyl- or triethylorthoacetate or propionate to give the corresponding trifluoromethylthiotrialkoxyethane or propane:

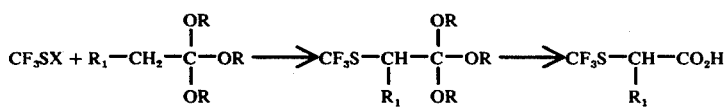

Formula I in which X is halo, especially fluoro or chloro; $R_1$ is hydrogen or methyl, and R is methyl or ethyl.

The condensation reaction proceeds in an organic solvent in which the reactants are substantially soluble and which, of course, is liquid at the reaction temperature. Most useful are ether, carbon tetrachloride, chloroform, tetrahydrofuran, ethyl acetate, methyl acetate, ethers of ethylene glycol, methylene chloride and acetonitrile. The temperature of the reaction mixture is usually from about −15° C. to 5° C., but depending on the time of reaction the temperature can vary from about −20° C. to 10° C. The time of reaction may vary from almost immediate reaction to several hours. We suggest that a free radical mechanism of action is involved which explains the short reaction time of the claimed method. Even though the progress of the reaction depends on many variables, including time, solvent, and temperature which we have described in detail herein, other combinations of these factors beyond those described here may be found useful by those skilled in the art.

The desired product may be optionally isolated and purified by standard methods as exemplified hereafter. Yields of 75–89% of purified product are common.

Another part of this invention are the intermediates of Formula I, above. As far as we are aware these are new organic compounds. The prior art had previously reported somewhat related compounds with two trifluoromethylthio groups substituted, J. F. Harris et al., J. Org. Chem., 32; 2063 (1967).

The intermediate trifluoromethylthiotrialkoxyalkane of Formula I is hydrolyzed most advantageously by reacting with a concentrated mineral acid at from about 60°–100° C. most usefully at the reflux temperature of the reaction mixture. A large excess of the acid of course is used. The term "concentrated mineral acid" is one known to the art. For example, hydrobromic, hydrochloric, hydriodic, sulfuric, phosphoric or perchloric acids. The hydrohalic acids are most easily used. The concentrations may vary from about 5N up to concentrated acid; the standard term "concentrated" is understood to represent common commercial strengths.

The reaction may be aided considerably by the presence of a catalytic amount of alkali metal iodide, such as sodium or potassium iodide. This may be due to the displacement nature of the reaction which is described herein as a hydrolysis reaction for convenience, or the removal of methyl or ethyl halides by distillation from the hydrolysis reaction.

The reaction time most conveniently may run at from one-half to five hours at reflux temperature.

Alternatively, the substituted orthoester, Formula I, may be hydrolyzed in two steps; first to the methyl or ethyl ester with an acid such as an anhydrous organic acid such as methylsulfonic, trifluoro acetic, ethereal hydrochloric or ethereal hydrobromic acids, then a standard alkali or strong acid hydrolysis to the free acid.

The yields of the key reactions for example using trimethylorthoacetate in the condensation reaction using trifluoromethylsulfenyl chloride followed by hydrolysis of the trimethoxy intermediate (I where R is methyl and $R_1$ is hydrogen) by 48% hydrobromic or 35% hydrochloric acid in the presence of sodium iodide gives from 50–55% yields.

The following examples are intended to teach specific instances of the use and utility of this invention.

EXAMPLE I

1-Trifluoromethylthio-2,2,2-trimethoxyethane (I):

A tared 500 ml. flask containing trimethylorthoacetate (96 g., 0.80 m.) in ether (240 ml.) was cooled in an ice methanol bath to −5° C. A constant stream of trifluoromethylsulfenyl chloride was bubbled into this stirred solution of ½ hour; weight increase 70 g. (0.51 m.). At that time a white precipitate was present. Additional trimethylorthoacetate (12 g., .01 m.) was added and the solution stirred and allowed to reach room temperature (one and one-half hours). The solid (7.0 g.) was filtered and rinsed with ether. The solvent and excess orthoacetate were removed (rotovap) and the infrared and NMR spectra of the resulting liquid (92.8 g.) were in agreement with I.

The product was distilled at the aspirator using an ice water cooled condensor. The main fraction, 62° C./15 mm. weighed 87.0 g. (0.395 m., 77.5% from sulfenyl halide), $n_D^{25}$ 1.3915. Trifluoromethylthioacetic Acid (II) with Hydrobromic Acid The orthoester I (20 g., 0.091 m.), 48% hydrobromic acid (130 ml.) and sodium iodide (1.0 g.) were refluxed for three hours. A few crystals of sodium thiosulfate were added, and the solution was saturated with solid sodium choride. The product was extracted with benzene and benzene-ether and the organic layer was dried with sodium sulfate, and the solvent removed on a rotovap.

The product was distilled 80° C./10 mm. and the main fraction weighed 10.0 g. (0.0625 m., 69%). Titration for COOH, 100.6%; $n_D^{25}$ 1.3917. With Hydrochloric Acid The orthoester I (5 g., 0.022 m.), concentrated hydrochloric acid (30 ml.) and sodium iodide (0.12 g.) were refluxed for three hours. The pink color was discharged with sodium thiosulfate and the solution treated with solid sodium chloride. Extraction as above gave a crude product, 2.9 g. (0.018 m., 82%) whose infrared spectrum was nearly identical to distilled II.

EXAMPLE II

A 5 L three-necked flask was equipped with a thermometer, a stirrer, an acetone-dry ice condenser, and a glass inlet tube. Into this flask was placed 3.3 kg. (27 moles) of trimethylorthoacetate. The reaction was cooled to −10° C. and trifluoromethylsulfenyl chloride gas metered into the flask. Reaction appeared to occur immediately with concurrent slight temperature increase. Temperature was maintained at −5 to −10° C. throughout the one and one-quarter hours required for the delivery of trifluoromethylsulfenyl chloride gas (695 g. 5.1 moles).

The dry ice acetone condensor was then replaced by a distillation set up whose trap is chilled −78° C. The reaction solution was warmed to 40° C. for one-half hour so as to purge the solution of any unreacted gas.

The solution was finally fractionally distilled at reduced pressure, 15–25 minutes at 25–30° C. The residue, 865 g., was collected for the subsequent hydrolysis.

A 12 L three-necked flask was equipped with a thermometer, a stirrer, a heating mantle and a 3 foot condenser connected to a dry ice acetone trap. Concentrated hydrobromic acid (48%) was poured into the flask and the adduct slowly added with stirring. The mixture was heated to 70° C. and stirred for three hours. Methyl bromide evolved and was trapped in the chilled bath.

The brown mixture was cooled to room temperature, saturated with sodium chloride and extracted with methylene chloride (3 L + 1.5 L + 1.5 L).

The methylene chloride solution was dried with sodium sulfate and the solvent evaporated under vacuum. The crude product was distilled at 3.5 mm., 51–52° C. to give 450 g. final product.

EXAMPLE III

A mixture of 15 g. of triethylorthopropionate in ether was cooled to −−5° C. then about 40 ml. of trifluoromethylsulfenyl chloride bubbled into the cooled reactant solution. After stirring at 10°–25° C. for ½ hour, the mixture was stripped to give 10 g. of the triethoxy product having consistent NMR and IR peaks (54.9%).

A mixture of 8 g. of the condensation product in 60 ml. of 48% hydrobromic acid with 0.05 g. of sodium iodide was heated at reflux (80°–100° C.) for 3 hours. The ether was allowed to evaporate. After cooling, salt was added and the mixture was extracted with benzene. The extract residues were distilled to give the desired α-trifluoromethylthiopropionic acid (80°–82° C. at the water aspirator).

What is claimed is:

1. The method of preparing a compound of the structure:

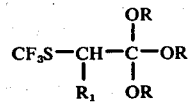

in which R is methyl or ethyl, and $R_1$ is hydrogen or methyl comprising reaction of a trifluoromethylsulfenyl halide with a compound of the structure:

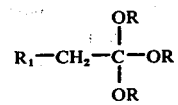

in which $R_1$ and R are as defined above.

2. The method of claim 1 in which the halide is the chloride.

3. The method of claim 2 in which $R_1$ is hydrogen and R is methyl.

4. The method of claim 3 in which the reaction temperature is within the range of from about −15 to 5° C.

5. The method of claim 4 in which the solvent is ether, methyl acetate, chloroform or carbon tetrachloride.

6. The method of preparing the trifluoromethylthio acetic or α-trifluoromethylthiopropionic acid comprising:

1. reacting a compound of the structure:

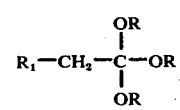

in which $R_1$ is hydrogen or methyl and R is methyl or ethyl with trifluoromethylsulfenyl chloride to give a trialkoxy compound of the structure:

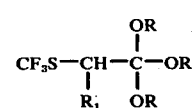

in which R and $R_1$ are as defined above, then 2. reacting said trialkoxy compound at reflux temperature with a concentrated strong inorganic acid.

7. The method of claim 6 in which $R_1$ is hydrogen and R is methyl.

8. The method of claim 6 in which a catalytic amount of an alkali metal iodide is present during the second reaction.

9. The method of claim 6 in which the inorganic acid is 47% hydrobromic acid or 35% hydrochloric acid.

10. The compound of the structure:

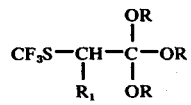

in which $R_1$ is hydrogen or methyl and R is methyl or ethyl.

11. The compound of claim 10 in which $R_1$ is hydrogen and R is methyl.

12. The compound of claim 10 in which $R_1$ is methyl and R is ethyl.

* * * * *